United States Patent [19]

Panton-Moore

[11] 4,342,743

[45] Aug. 3, 1982

[54] PREPARATION FOR THE CARE AND CONDITIONING OF THE FEET

[76] Inventor: Lithia Panton-Moore, 570 Lefferts Ave., 2D, Brooklyn, N.Y. 11203

[21] Appl. No.: 237,740

[22] Filed: Feb. 24, 1981

[51] Int. Cl.³ .................. A61K 7/04; A61K 37/48
[52] U.S. Cl. ................................. 424/61; 424/94
[58] Field of Search .................. 424/94, 153, 61, 154

[56] References Cited

U.S. PATENT DOCUMENTS

| | | | |
|---|---|---|---|
| 673,769 | 5/1901 | Ford | 424/154 |
| 711,263 | 10/1902 | Robertson | 424/154 |
| 1,160,317 | 11/1915 | Perine | 424/153 |
| 1,465,530 | 8/1923 | Smith | 424/153 |
| 1,716,686 | 6/1929 | Crossley | 424/154 |
| 2,073,659 | 3/1937 | Stratton | 424/94 |
| 3,019,171 | 1/1962 | Block et al. | 424/94 |
| 3,062,721 | 11/1962 | Grate | 424/347 |
| 4,014,995 | 3/1977 | Juliano et al. | 424/195 |
| 4,108,984 | 8/1978 | Sato | 424/94 |

FOREIGN PATENT DOCUMENTS

863538  3/1961  United Kingdom .

*Primary Examiner*—Donald B. Moyer
*Attorney, Agent, or Firm*—James J. Romano, Jr.

[57] ABSTRACT

A new and improved preparation for the care and conditioning of the feet is provided and comprises magnesium sulphate, natural sea and land salts, a papaya enzyme and salicylic acid which, when mixed to form a powder and dissolved in warm or hot water, provides a soothing and comforting soak for the feet, and one which is particularly conducive to the subsequent removal of dead tissue in the nature of callouses and the like therefrom through softening of that dead tissue.

8 Claims, No Drawings

PREPARATION FOR THE CARE AND CONDITIONING OF THE FEET

BACKGROUND OF THE INVENTION

1. Field of the Invention

This invention relates to a new and improved preparation for the care and conditioning of the feet and, more particularly, to such preparation as may be readily and economically formulated and utilized to provide a wide variety of meaningful benefits.

2. Description of The Prior Art

Although a wide variety of preparations for the care of the feet are, of course, known in the prior art, no prior are preparation of this nature is known to applicant to have the same ingredients as the preparation of the invention, or to provide the variety of significant benefits as are provided by the preparation of the invention. More specifically, among those currently available foot care preparations known to applicant as a result of a particularly comprehensive survey thereof are: (a) "Johnson's Foot Soap" by Combe Incorporated of White Plains, N.Y. 10604; (b) "Gill's Foot Soap" by Thomas Gill Soap Co. of White Plains, N.Y. 10604; (c) "Footherapy" by Para Laboratories, 100 Rose Avenue, Hempstead, N.Y. 11550; (d) "Soap 'n Soak" by Scholl, Inc., Chicago, Ill. 60610; (e) "Pretty Feet" by Norcliff-Thayer Co. believed also to be of Chicago, Ill.; (f) "Jovan Foot Care Kit" by Jovan, Inc., 875 North Michigan Avenue, Chicago, Ill. 60611; (g) "Foot Spa Cattier Foot Care Product" by The Pierre Cattier Co., 16 Hudson Street, New York, N.Y. 10013; (h) "Sof-Foot" by Sunset Glare Guard Corp., P.O. Box 1209, Palm Springs, Calif. 92262; and (i) "Barielle" by Benson Wilkes, Inc. 598 Madison Avenue, New York, N.Y. 10022. In each instance, detailed review and consideration of the ingredients, purchase price and/or instructions for use of these prior art foot care preparations, as provided on the preparation package or label, and/or carefully controlled actual test of the prior art foot care preparation in question, reveal those preparations not to have the same ingredients or combination of ingredients as the foot care preparation of this invention, to command a significantly higher purchase price than that envisaged for the foot care preparation of this invention, to require significantly more frequent use than the foot care preparation of this invention, and/or not to, in any event, provide the multitudinous beneficial effects as are provided by the foot care preparation of this invention. Too, certain of the prior art foot care preparations known to applicant as specified hereinabove contain active ingredients or combinations thereof which can cause harmful side-effects and which could, if accidentally ingested as for example by a small child, cause consequential illness to thus require particular care in the use and storage of those prior art foot care preparations in the home and to, in any event, introduce an unnecessary element of risk attendant the use of those preparations.

OBJECTS OF THE INVENTION

It is, accordingly, an object of my invention to provide a new and improved preparation for the care of the feet which provides a wide variety of meaningful benefits to the user thereof.

Another object of my invention is the provision of a new and improved foot care preparation as above which requires the use of only readily available ingredients of proven dependability and efficacy, and which requires only the simple mixing of those ingredients in the formulation of the preparation.

Another object of my invention is the provision of a new and improved foot care preparation as above which, because of the nature of the ingredients and the manner of formulation, may be formulated at relatively low cost.

Another object of my invention is the provision of a new and improved foot care preparation as above which is particularly simple to utilize.

A further object of my invention is the provision of a new and improved foot care preparation as above which contains no inherently toxic or otherwise harmful ingredients or combination(s) thereof, and which may be used without adverse side-effects, to thus provide for a maximal degree of safety in the storage and use of the preparation in the home.

A still further object of my invention is the provision of a new and improved foot care preparation as above which, because of its high degree of efficacy, need only be utilized at relatively infrequent intervals to maintain a likewise high degree of beneficial foot care and conditioning.

SUMMARY OF THE DISCLOSURE

As disclosed herein, the new and improved preparation of my invention for the care and conditioning of the feet will preferably comprise primarily magnesium sulphate, natural sea and land salts, a papaya enzyme, and salicylic acid which are respectively mixed to form a powder. In use, this powder is dissolved in an appropriate quantity of warm or hot water and the feet soaked therein for an appropriate time period to thoroughly cleanse the same and break down and soften calloused foot tissue and the like and to provide a generally soothing and pleasant feeling to the feet. Thereafter, the thusly softened calloused tissue and the like may advantageously be readily removed from the feet by simply sloughing the same off with a podiatric stone or like implement. Additionally, included in the preparation may be green clay, colloidal oatmeal, chlorophyll and a dye to respectively smooth out the same and provide a more pleasant feeling and an agreeable odor and attractive appearance thereto. Although the proportions of the ingredients may vary, a general range thereof would be two parts of the magnesium sulphate to one part of all of the other ingredients, with the exception of the chlorophyll and the dye which are included in relatively small quantities for appearance-improving functions.

DETAILED DESCRIPTION OF THE INVENTION

The significant importance of the proper care of the feet from both physiologic and cosmetic standpoints is becoming more readily recognized.

Specifically, from a physiologic standpoint, it is clear that those suffering from feet which are, for example, excessively calloused or the like tend to experience persistent discomfort, and will often suffer pain as well. Such discomfort, and/or pain which may be quite extreme for some people, interferes greatly with a feeling of well-being. Moreover, such discomfort often contributes to abnormal walking patterns and faulty weight distribution which, in turn, contribute to muscular fatigue. Foot fatigue also generally contributes to what is commonly termed that "tired" feeling; and that "tired" feeling contributes in turn to a less-than-sunny disposition.

In addition, foot problems of the nature discussed hereinabove can, in instances where occupational requirements place excessive demands on the feet, even interfere with one's occupation and/or livelihood. People who fall into this category are, for example, mailpersons, policepersons, salespersons, dancers and the like.

Also, with the remarkable current interest in popularity of, in reality craze for, such foot-dependent recreational activities as jogging, competitive long distance running, and even street skating for adults, it is equally clear that foot problems of the nature under discussion are by no means limited to those in foot-dependent occupations.

From a cosmetic standpoint, it is clear that increasing emphasis is currently being placed by society upon the overall appearance of the body, including, of course, that of the feet. In addition, the importance of the erotic aspects of the feet, especially to women, is also of course becoming more clearly understood and widely recognized. Under these circumstances, it can be readily understood that one suffering, for example, from excessively calloused feet or the like which might generally be considered as "ugly," can and would be at a not insignificant disadvantage in an increasing number of personal and social situations. This problem would, for example, be particularly acute for a black woman with excessively calloused feet or the like which would present an "ashy" appearance due to the greater contrast in coloration between dead tissue and dark skin. Additionally, from a practical standpoint, calloused feet are particularly costly for woman since they readily and effectively tear sheer hosiery and pantyhosiery which are expensive.

The significant importance of the proper care and conditioning of the feet from both physiologic and cosmetic standpoints is made even clearer by the following publications: (a) *Foot Notes* by M. Arnot, published in 1980 by Doubleday and Company, Inc., New York, N.Y.; (b) *About Feet* by H. Day, published in 1971 by Weatherby, Woolnough Ltd., Northants, Great Britain; (c) *Stories the Feet Have Told* by E. D. Ingham, published in 1951 and 1963 by Ingham Publishing, Rochester, N.Y.; (d) *A Doctor Discusses Care of the Feet* by S. Berkman in conjunction with V. C. D'Amico, D.P.M. and S. Springer, M.D., published in 1979 by Budlong Press Co., New York, N.Y.; (e) *Helping Yourself with Foot Reflexology* by M. Carter, published 1969 through 1979 by Parker Publishing Company, Inc., West Nyack, N.Y.; (f) *An everyday guide "To Your Health"* by D. S. Sobel and F. L. Hornbacher, published in 1973 by Grossman Publishers, New York, N.Y.; and *Handbook of Non-Prescription Drugs* by F. Sadik, Ph.D., published in 1971 by the American Pharmaceutical Association.

In accordance with the teachings of this invention, the ingredients of my new and improved preparation for the care and conditioning of the feet will, as currently contemplated, comprise: magnesium sulphate; sea salt taking for example the form of solar dried sodium chloride with magnesium carbonate; natural land salt taking for example the form of sodium chloride marketed as "Natural Indian Mount Land Salt" by Indian Mount Bald Mountain Formulations of Mineral Wells, Texas, papaya enzyme and salicylic acid.

More preferably, these ingredients will further comprise: green clay taking for example the form of that marketed by Pierre Cattier Company, New York, N.Y. which includes silica, iron, calcium, magnesium, sodium, manganese, potassium, chloride and zinc; and colloidal oatmeal.

Most preferably, these ingredients will further comprise: chlorophyll in, for example, powdered form; and an appropriate natural dye, for example a natural green vegetable dye to render the preparation more pleasing to the eye.

In accordance with the teachings of this invention, the proportions for the ingredients of my new and improved preparation for the care and conditioning of the feet will, as currently contemplated, be by volume approximately: two parts magnesium sulphate; one part sea salt; one part papaya enzyme; one part salicylic acid; one part green clay; one part colloidal oatmeal; one part land salt; and appropriate small quantities of chlorophyll and dye for odor control and eye appeal functions as discussed in greater detail hereinbelow.

More preferably, these proportions for the preparation ingredients will be by volume approximately: two parts magnesium sulphate; one part sea salt; one part papaya enzyme; one part salicylic acid; one part green clay; one-half part land salt; one-half part colloidal oatmeal; and appropriate small quantities of chlorophyll and dye.

Most preferably, these proportions for the preparation ingredients will be by volume approximately: five parts magnesium sulphate; two parts sea salt; one part land salt; three parts papaya enzyme; three parts salicylic acid; two parts green clay; one and one-half parts colloidal oatmeal; and appropriate small quantities of chlorophyll and dye.

For use, and with each of the last-mentioned proportional parts being equal to, for example, one tablespoon of the relevant ingredient, and all of the ingredients being mixed as through use, for example, of a mortar and pestle to form a uniform powder which may be pre-packaged as one foot treatment preparation portion, it may be understood that the thusly constituted preparation of the invention is simply added to and thoroughly mixed with an appropriate quantity, for example, two quarts, of warm or hot water in which the preparation will rapidly and substantially dissolve. Thereafter, the feet are simply immersed in the thusly prepared solution and soaked therein for an appropriate time period, for example 20 to 30 minutes, and then removed therefrom.

In addition to the generally soothing, comforting and relaxing feeling imparted to the feet by soaking as described in the solution of the invention, it may be understood that the same will also most advantageously function to thoroughly cleanse the feet by softening and separating therefrom any dirt or other foreign matter thereon, and will also most advantageously function to very materially soften any and all dead tissue in the nature of callouses or the like thereon. In this latter regard, it may be more specifically understood that the magnesium sulphate and salicylic acid will naturally soften this dead tissue; with the land and sea salt promoting the absorption of water by the dead tissue to further induce the softening thereof, and the natural protein digesting action of the papaya enzyme further assisting in the break-down and softening of the dead tissue. In addition, the green clay and colloidal oatmeal will in essence impart a smoother, more pleasant feeling to the solution, while the chlorophyll and dye will render the same pleasing to the nose and eye.

Following soaking of the feet as above, the solution of the invention is simply discarded, and the feet re-soaked if desired in a like quantity of warm or hot water to which a small quantity of liquid soap or the like has been added for a suitable and comfortable time period. Thereafter, the feet are removed from this additional soak, and an appropriate implement in the nature, for example, of a podiatric stone gently rubbed thereover with a circular motion, concentrating of course on the more heavily calloused areas, to simply slough off the dead tissue and the like, as have been advantageously softened by the preparation of the invention, and restore the feet to a more healthful condition. Further, it is desirable that, following the use as described of the preparation of my invention, the feet be massaged with an appropriate, naturally soothing cream containing, for example, oil of wintergreen. Massaging the feet with such cream will contribute even further to the foot comforting and restorative process and impart a pleasant softness and feeling of lightness and comfort to the feet.

Although frequency of use of the new and improved foot care and conditioning preparation of my invention will, of course, vary depending upon the extent of the relevant foot problems of the user, it is believed that one utilization thereof as described every two weeks should prove quite sufficient as a general average.

Actual, comprehensive and carefully controlled tests of the new and improved preparation of my invention have proven the same particularly effective for the purposes disclosed and to have no discernible, harmful side effects. In addition, and considering the basically non-toxic and non-reactive nature of the preparation ingredients, and the relatively small amounts thereof as are included in each treatment portion, it is believed that the preparation is so safe as to probably be ingestable without particularly serious consequence although, of course, such action would never be advised.

Various changes may of course be made in the foot care and conditioning preparation of my invention as disclosed herein without departing from the spirit and scope of that invention as defined by the appended claims.

What is claimed is:

1. In a preparation for mixture with water to form a foot-soak solution in which the feet may be soaked to sooth, comfort, relax and cleanse the feet, and soften the dead calloused skin tissue to facilitate the removal thereof, the improvements comprising, in combination by volume, about two parts magnesium sulphate, about two parts sodium chloride, about one part papaya enzyme, and about one part salicylic acid.

2. In a preparation as in claim 1 wherein, said sodium chloride is in the form of natural land and sea salts 3. In a preparation as in claim 1 further comprising, in combination by volume, about one part green clay, and about one part colloidal oatmeal.

4. In a preparation for mixture with water to form a foot-soak solution in which the feet may be soaked to sooth, comfort, relax and cleanse the feet, and soften dead calloused skin tissue to promote and facilitate the removal thereof, the improvements comprising, in combination by volume, about five parts magnesium sulphate, about three parts sodium chloride, about three parts papaya enzyme, and about one part salicylic acid.

5. In a preparation as in claim 4 wherein, said sodium chloride is in the form of a mixture of natural land and sea salts.

6. In a preparation as in claim 5 wherein, said natural land and sea salts are in the proportion by volume of about two parts sea salt to about one part land salt.

7. In a preparation as in claim 4 further comprising, in combination by volume, about two parts green clay, and about one and one-half parts colloidal oatmeal.

8. In a preparation as in claim 7 further comprising, in combination by volume, minimal quantities of chlorophyll and a natural dye.

* * * * *